(12) United States Patent
Krupa et al.

(10) Patent No.: US 6,991,603 B2
(45) Date of Patent: Jan. 31, 2006

(54) INSERTION TUBE DEVICE

(75) Inventors: Robert J. Krupa, Leominster, MA (US); William F. Laflash, Northbridge, MA (US); Matthew G. Maher, Worcester, MA (US); Thomas V. Root, Beverly, MA (US); Ralph C. Tillinghast, Worcester, MA (US)

(73) Assignee: Optim, Inc., Sturbridge, MA (US)

( * ) Notice: Subject to any disclaimer, the term of this patent is extended or adjusted under 35 U.S.C. 154(b) by 180 days.

(21) Appl. No.: 10/150,454

(22) Filed: May 17, 2002

(65) Prior Publication Data

US 2003/0216616 A1 Nov. 20, 2003

(51) Int. Cl.
*A61B 1/00* (2006.01)

(52) U.S. Cl. ...................... 600/141; 600/139; 600/920; 138/119

(58) Field of Classification Search ................ 600/139, 600/141, 920; 138/119, 123–127, 133; 604/523
See application file for complete search history.

(56) References Cited

U.S. PATENT DOCUMENTS

| 6,083,152 A * | 7/2000 | Strong ........................ 600/139 |
| 6,206,824 B1 * | 3/2001 | Ohara et al. ................. 600/139 |
| 6,273,880 B1 * | 8/2001 | Berg et al. ................... 604/523 |
| 6,503,193 B1 * | 1/2003 | Iwasaki et al. ............. 600/140 |
| 6,520,214 B1 * | 2/2003 | Sugiyama et al. .......... 138/119 |
| 2001/0056224 A1 | 12/2001 | Renner et al. |

* cited by examiner

Primary Examiner—Beverly M. Flanagan
(74) Attorney, Agent, or Firm—Proskauer Rose LLP

(57) ABSTRACT

Insertion tube devices are disclosed.

69 Claims, 4 Drawing Sheets

INSERTION TUBE DEVICE

TECHNICAL FIELD

The invention relates to insertion tube devices.

BACKGROUND

Insertion tube devices are commonly used in medical applications and non-medical applications. Typically, medical insertion tube devices are used to deliver and protect visual and/or medical devices in a patient (e.g., a human patient). Examples of medical insertion tube devices include endoscopes (e.g., laparascopes, colonoscopes, sigmoidoscopes) and catheters. Often, non-medical insertion tube devices are used to inspect relatively difficult to view places, such as mining drill holes, interior of an aircraft engine, or pipes. Examples of non-medical endoscopes include borescopes and fiberscopes.

SUMMARY

In general, the invention relates to insertion tube, catheter, and umbilical devices.

In one aspect, the invention features a method that includes disposing a substantially unmelted first material adjacent a surface of a base material. The method also includes melting at least a portion of the first material, and solidifying the portion of the first material so that the first and base materials form a flexible member in which the first material is at least partially bonded to the surface of the base material.

In another aspect, the invention features a method that includes disposing a substantially unmelted first material adjacent a surface of a base material. The method also includes bonding at least a portion of the first material to the surface of the base material to form a flexible member without extruding the first material onto the surface of the second material.

In a further aspect, the invention features a method that includes disposing a substantially unmelted first material adjacent a surface of a base material. The method also includes melting at least a portion of the first material, and solidifying the portion of the first material so that the first and base materials form a shaft of an insertion tube device in which the first material is at least partially bonded to the surface of the base material.

In another aspect, the invention features a method that includes disposing a substantially unmelted first material adjacent a surface of a base material. The method also includes bonding at least a portion of the first material to the surface of the base material to form a shaft of an insertion tube device without extruding the first material onto the surface of the second material.

In a further aspect, the invention features a flexible member that includes a base material and a first material. A first portion of the first material forms a layer adjacent the surface of the base material, and a second portion of the first material is disposed within the base material at discrete locations. The flexible member is configured to be inserted into a cavity of a patient.

In another aspect, the invention features a shaft of an insertion tube device. The shaft includes a base material and a first material. A first portion of the first material forms a layer adjacent the surface of the base material, and a second portion of the first material is disposed within the base material at discrete locations. The shaft is configured to be inserted into a cavity of a patient.

In another aspect, the invention features a method that includes disposing a substantially unmelted first material adjacent a surface of a base material having openings. The method also includes melting at least a portion of the first material into the openings of the base material, and solidifying the portion of the first material so that the first and base materials form a flexible member in which the first material is at least partially disposed within the openings in the base layer.

In one aspect, the invention features a method that includes disposing a substantially unmelted first material adjacent a surface of a base material having openings. The method also includes bonding at least a portion of the first material within the openings of the base material to form a flexible member without extruding the first material onto the surface of the second material.

In another aspect, the invention features a method that includes disposing a substantially unmelted first material adjacent a surface of a base material having openings. The method also includes melting at least a portion of the first material into the openings of the base material, and solidifying the portion of the first material so that the first and base materials form a shaft of an insertion tube device in which the first material is at least partially disposed within the openings in the base layer.

In a further aspect, the invention features a method that includes disposing a substantially unmelted first material adjacent a surface of a base material having openings. The method also includes bonding at least a portion of the first material within the openings of the base material to form a shaft of an insertion tube device without extruding the first material onto the surface of the second material.

In certain embodiments, the flexible member has a relatively long use life. For example, the flexible member can undergo relatively little delamination and/or wrinkling.

In some embodiments, the flexible member provides good crush resistance to reduce the likelihood of damage to the components (e.g., image transmission guide, optical guide) during use.

In certain embodiments, the shaft of the insertion tube device has a relatively long use life. For example, the shaft of the insertion tube device can undergo relatively little delamination and/or wrinkling.

In some embodiments, the shaft of the insertion tube device provides good crush resistance to reduce the likelihood of damage to the components contained in the shaft (e.g., image transmission guide, optical guide) during use.

Features, objects and advantages of the invention are in the description, drawings and claims.

DETAILED DESCRIPTION

Figure 1:
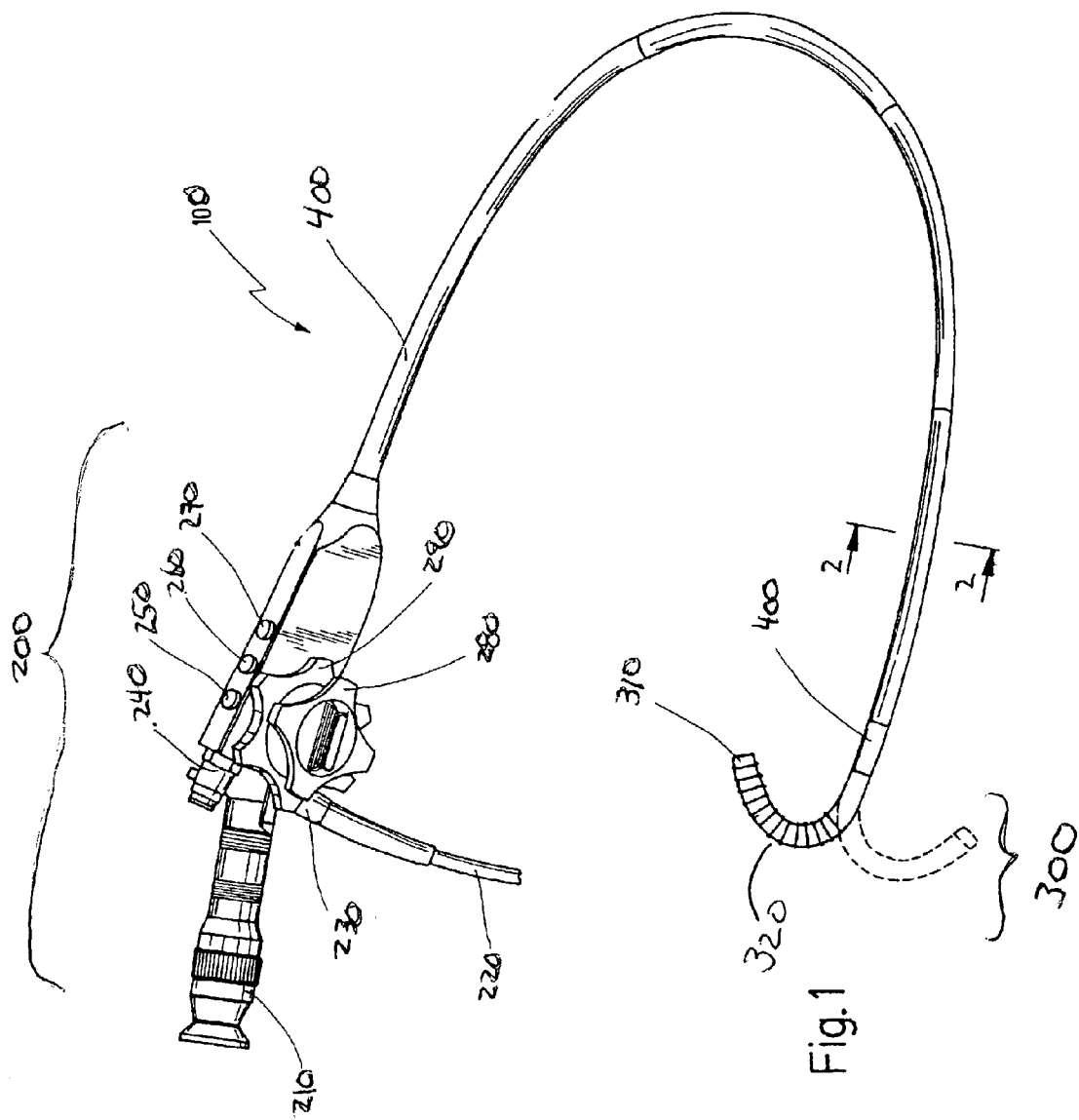
FIG. 1 is a perspective view of an embodiment of an endoscope.

FIG. 1 is a perspective view of a flexible endoscope 100 having a proximal end 200, a distal end 300, and a shaft 400.

Proximal end 200 includes an ocular 210, an umbilical 220, connectors 230 and 240, switches and/or valves 250, 260 and 270, and hand wheels 280 and 290. Umbilical 220 can house, for example one or more light guides (e.g., for transmitting illumination from a light source to an object adjacent end 300), electrical wires (e.g., for motorized components, such as articulation, valves), a video camera, components for a video camera, irrigation and/or suction and/or working channel(s) to house certain optical fibers.

Distal end 300 includes optics 310 (e.g., lens(es)) and bending section 320.

Figure 2:
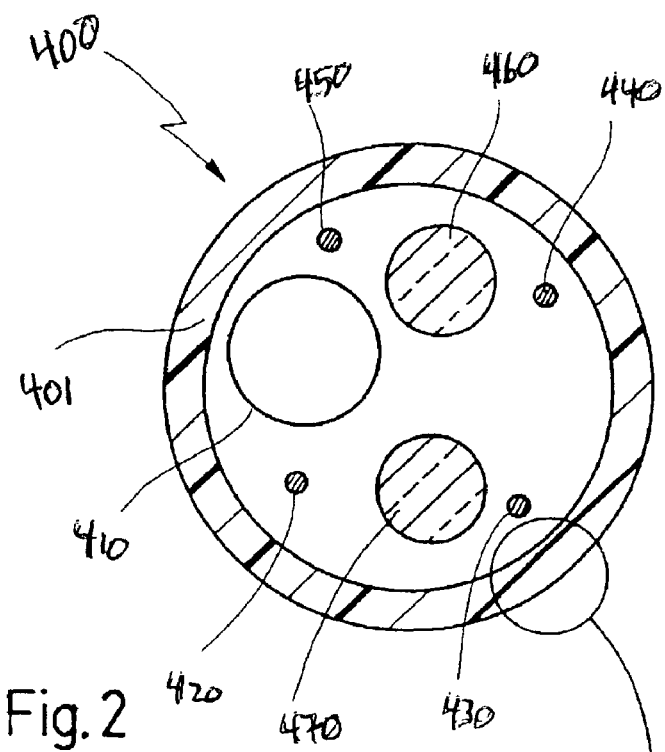
FIG. 2 is a cross-sectional view of an embodiment of a shaft of an insertion tube device.

FIG. 2 is a cross-sectional view of shaft 400. Shaft 400 (e.g., a mantle) includes a wall 401 that houses an instrument channel 410, steering cables 420, 430, 440 and 450, an image transmission guide 460, and an optical guide 470.

In general, shaft 400 has a relatively high hoop strength and provides good crush resistance. For example, shaft 400 can have a hoop strength of at least about 500 pounds per square inch (e.g., at least about 1,000 pounds per square inch, at least about 2,500 pounds per square inch, at least about 4,000 pounds per square inch) and/or at most about 10,000 pounds per square inch (e.g., at most about 7,000 pounds per square inch, at most about 5,000 pounds per square inch). The hoop strength of the shaft is measured by disposing the shaft on an anvil (e.g., 0.25 inch long by 0.03 inch wide anvil), and applying a force to the shaft with a force gauge. The hoop strength is calculated by measuring the force at which the shaft collapses and dividing this force by the area of the anvil.

Generally, shaft 400 has good flexibility. For example, shaft 400 can have a relatively small bending radius, which refers to the minimum radius that shaft 400 can be bent without rendering the components disposed within shaft 400 inoperable. In certain embodiments, shaft 400 has a bending radius of at least about one millimeter (e.g., at least about five millimeters, at least about 10 millimeters, at least about 25 millimeters, at least about 50 millimeters) and/or at most about 100 millimeters (e.g., at most about 75 millimeters).

In some embodiments, shaft 400 is configured for medical use, such as to be disposed within a cavity (e.g., colon, stomach, esophagus, bronchi, larynx, urethra, kidneys, bladder, ear, nose) of a patient (e.g., a human, an animal). Examples of devices with such shafts include a colonoscope (e.g., to examine the colon or large intestine), a gastroscope (e.g., to examine the stomach through the esophagus), and a cystoscope (e.g., to examine the bladder via insertion through the urethra).

In certain embodiments, shaft 400 is configured for non-medical use, such as to be disposed within a non-patient cavity (e.g., pipe, automobile gas tank, interior of an aircraft engine, interior of a metal or plastic casting). Examples of such shafts include a borescope that can be used to examine a pipe for clogs or buildup, to inspect an automobile gas tank for illegal items, to inspect the interior of an aircraft engine for foreign object damage, cracks, or fatigue, and/or to inspect the interior of a metal casting for cracks or voids.

The length of shaft 400 can be varied as desired. In certain embodiments, shaft 400 has a length of at least about 150 millimeters (e.g., at least about 250 millimeters, at least about 500 millimeters, at least about one meter, at least about 1.5 meters, at least about five meters, at least about ten meters). In certain embodiments in which shaft 400 is used in an otorhinolaryngoscope (e.g., for examining the ear, nose and/or throat) shaft 400 may have a shaft length of about 250 millimeters or less. In some embodiments in which shaft 400 is used in a colonoscope, shaft 400 can be about 1,700 millimeters long. In embodiments in which shaft 400 is used in an industrial borescope, shaft 400 can have a length of about 250 millimeters (e.g., for viewing relatively shallow cavities and/or tubes) or tens of meters (e.g., for inspecting mining drill holes and/or pipes).

The diameter of shaft 400 can also be varied as desired. In some embodiments, shaft 400 has a diameter of at least about one millimeter (e.g., at least about two millimeters, at least about five millimeters) and/or at most about 30 millimeters (e.g., at most about 20 millimeters, at most about 15 millimeters). In certain embodiments in which shaft 400 is designed to be used in a medical insertion tube device, shaft 400 can have a diameter of from about one millimeter to about 15 millimeters. In some embodiments in which shaft 400 is designed to be used in a non-medical insertion tube device, shaft 400 can have a diameter of from about one millimeter to about 30 millimeters.

Figure 3:
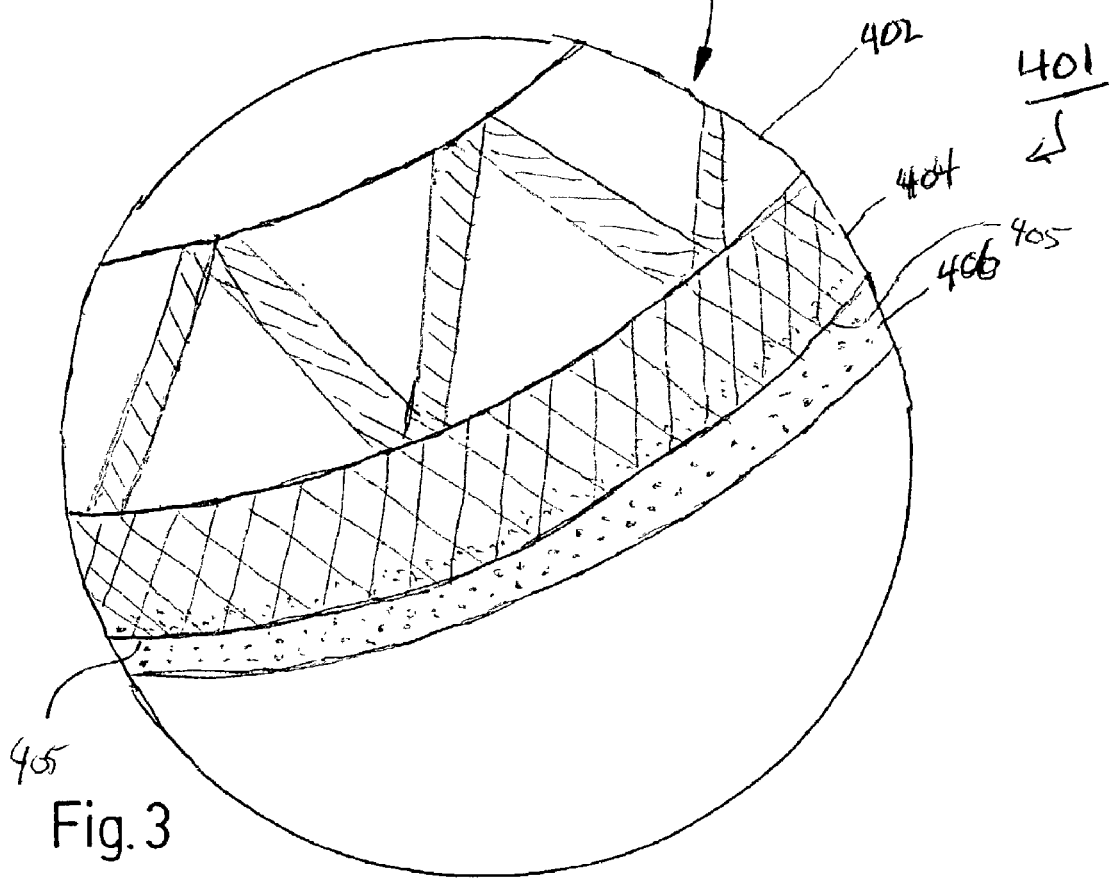
FIG. 3 is an enlarged, partial cross-sectional view of an embodiment of a wall of a shaft of an insertion tube device.

FIG. 3 is an enlarged, partial cross-section view of an embodiment of wall 401. Wall 401 includes a layer 402 formed of spiral (e.g., metal or polymer) made from a flat strip of material (monocoil), a layer 404 of braided material, and a urethane layer 406 bonded to and partially disposed within layer 404.

In some embodiments, the combined thickness of layers 402, 404 and 406 is at most about one millimeter (e.g., at most about 0.5 millimeter, at most about 0.3 millimeter). In some embodiments in which shaft 400 is used in an otorhinolaryngoloscope or a bronchoscope, the combined thickness of layers 402, 404 and 406 can be about 0.3 millimeter. In certain embodiments in which shaft 400 is used in a gastroscope or a colonoscope, the combined thickness of layers 402, 404 and 406 can be from about 0.7 millimeter to about one millimeter. In certain embodiments, as the length of shaft 400 increases, the combined thickness of layers 402, 404 and 406 increases.

Although layer 402 is shown as being formed as a monocoil, layer 402 can be formed in a different configuration. In general, layer 402 can have any configuration that enhances the hoop strength of shaft 400. Typically, such a configuration can be formed into a spiral that can be stretched. Materials from which layer 402 can be formed include, for example, a metal or polymer monocoil (flat spring), a double monocoil of metal or polymer, a spring with a round or oval cross section, a flexible conduit, or a flexible polymer tubing with enough wall thickness and strength to provide the desired hoop strength (e.g. PEBAX tubing, PTFE tubing).

While layer 404 is shown as being formed of a braided material, layer 404 can have a different configuration. Typically, layer 404 can have any configuration that assists in controlling the compression and/or extension of shaft 400. In some embodiments, layer 404 has an open structure so that the material of layer 406 can be at least partially disposed within layer 404. Examples of materials from which layer 404 can be formed include braid or mesh manufactured from, for example, metals, alloys, low-stretch polymers (e.g. nylon, Kevlar), fiberglass, and composites of these materials. Typically, the braid or mesh wire or thread has a round cross section, but other shaped cross-section can be used (e.g., flat, oval).

Layer 406 can be formed of any material capable of bonding to layer 404. In certain embodiments, layer 406 is formed of material that, when at least partially melted, can extend into layer 404 (e.g., extend into openings in layer 404). In some embodiments, layer 406 is formed of a polymer (e.g., an elastomer, a thermoplastic). Examples of polymers include urethanes, polyesters, olefinic thermoplastic elastomers, chlorinated polyethylene-based thermoplastic elastomers, polyvinyl chlorides, 1,2-butadienes, polystyrenes, fluoropolymer-silicon rubber materials (e.g., Sil-Kore from W. L. Gore), and fluoropolymers (e.g., Viton from DuPont, HSTS from W. L. Gore).

Figure 4:
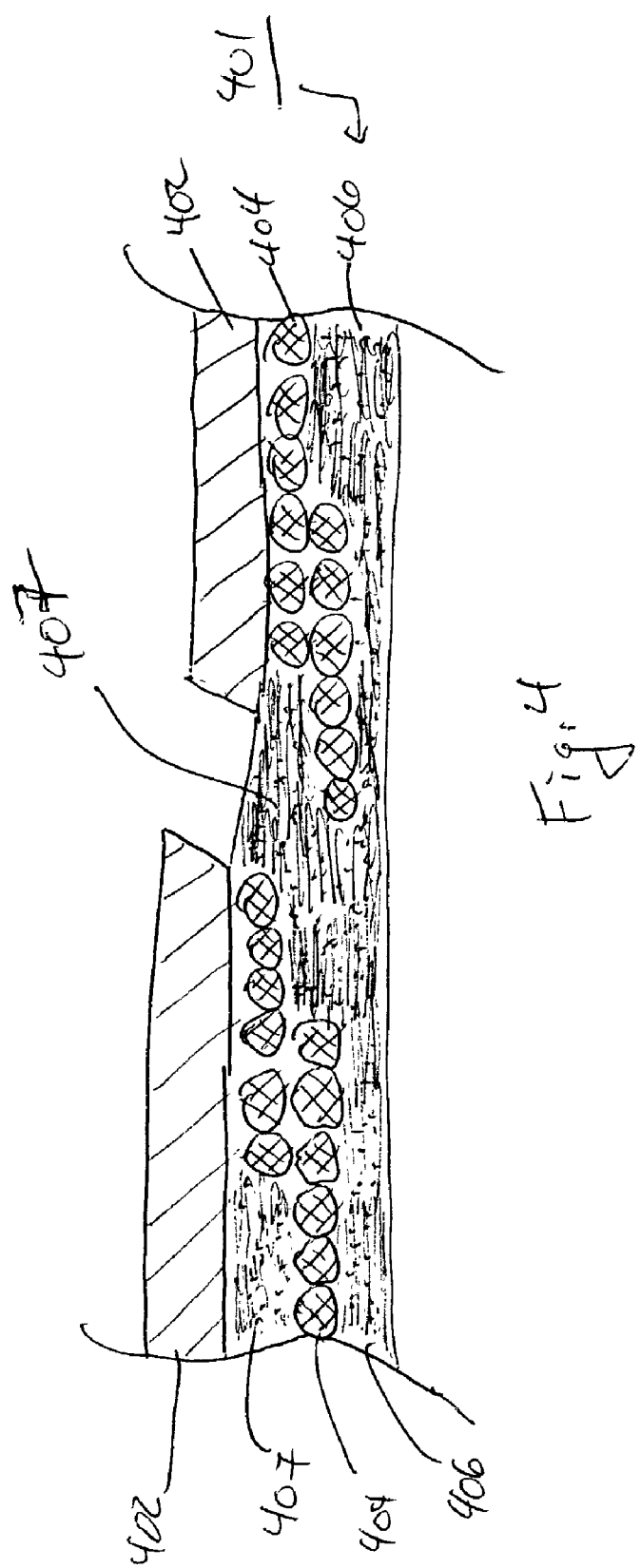
FIG. 4 is an enlarged, partial cross-sectional view of an embodiment of a wall of a shaft of an insertion tube device.

Typically, layer 406 is bonded to layer 404 along a surface 405 of layer 406. As shown in FIG. 3, a portion of the material of layer 406 can extend into openings in layer 404. In some embodiments, the portion of the material of layer 406 that extends into layer 404 can be relatively evenly distributed throughout layer 404. In certain embodiments, at least some of the portion of the material of layer 406 that extends into openings in layer 404 forms discrete locations (e.g., mushroom-shaped entities, rivet-shaped entities) within layer 404 that provide particularly strong bonding between layer 404 and the material of layer 406. FIG. 4 shows a partial cross-sectional view of an embodiment of wall 401 in which a portion of the material of layer 406 that extends into layer 404 forms discrete locations 407 in the openings in layer 404. In some embodiments, locations 407 extend into openings in layer 402.

In some embodiments, the portion of the material of layer 406 extends into openings in layer 404 a distance that is at least about five percent (e.g., at least about 10%, at least about 20%) of the thickness of layer 404. For example, in embodiments in which layer 404 is formed of a braid of wire (e.g., stainless steel braid wire) having a diameter of from about 0.001 inch to about 0.005 inch, a portion of the material of layer 406 can extend into layer 404 a distance of at least about 0.001 inch (e.g., at least about 0.005 inch, at least about 0.01 inch, about 0.012 inch).

Figure 5:
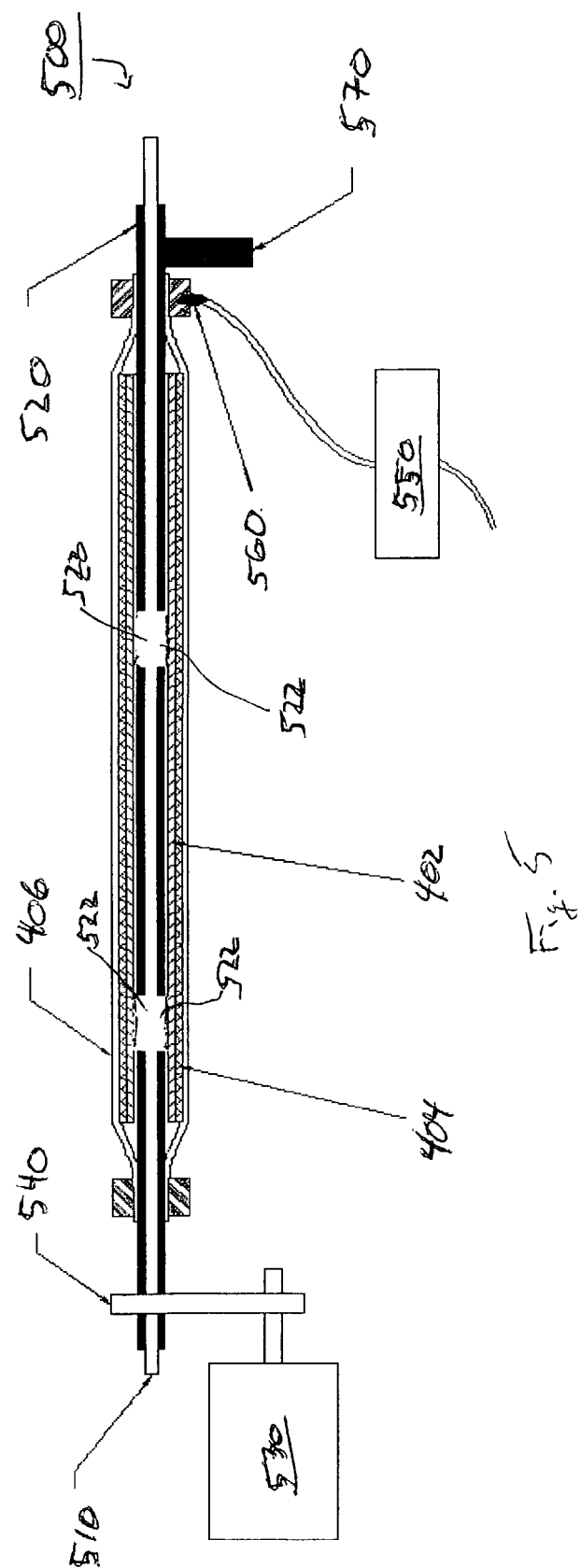
FIG. 5 is a cross-sectional view of an embodiment of a system for forming a shaft of an insertion tube device.

FIG. 5 is a cross-sectional view of a system 500 for forming a shaft of an insertion tube device. System 500 includes a heating element 510, a stainless steel tube 520 having openings 522, a motor 530, a drive belt 540, a temperature controller 550, a thermocouple 560, and a port 570 to a vacuum pump.

Layers 402, 404 and 406 (in a substantially unmelted state) are disposed adjacent each other as shown. Heating element 510 (e.g., a resistive heater rod) is disposed within stainless steel tube 520, and these components are placed inside layer 402. Motor 530, belt drive 540, temperature controller 550 (e.g., a programmable temperature controller) and thermocouple 560 are then connected within system as shown.

An electrical potential is placed across heating element 510, causing it to heat up, which, in turn, causes stainless steel tube 520 to heat up. The relatively low thermal conductivity of stainless steel tube 520 assists in more evenly distributing the heat to layers 402, 404, 406, thereby reducing the formation of localized hot spots. As layer 406 heats up, at least some (e.g., all) of the material (e.g., urethane) from which layer 406 is formed melts. A vacuum is applied to the interior of layer 402 via port 570 and openings 522, which causes some of the melted material to flow into the openings of layer 404. At the same time, motor 530 powers belt drive 540, which rotates the elements of system 500 (e.g., at a rate of about 25 revolutions per minute), except for heating element 510. Rotation can assist in creating an even flow of layer 406, improving the exterior surface appearance after cooling of layer 406, producing a uniform wall thickness of layer 406, and/or a more uniform heating of the assembly by heating element 510

The electrical potential is removed from heating element 510, and element 510 is then allowed to cool. The components of the system can be disposed within a container during the cooling process to reduce exposure to rapid changes in ambient air temperature, dust and/or other debris. As the melted material of layer 406 cools, it bonds to the material of layer 404. In certain embodiments, a portion of the material of layer 406 can be present within openings in layer 404 (see discussion above).

Layers 402, 404 and 406 are then removed from the system and trimmed to the desired length.

In some embodiments, a pressure is applied to the exterior of layer 406, rather than applying a vacuum to the interior of layer 402, to enhance the flow of a portion of the material of layer 406 into layer 404. The system can be constructed without a vacuum port 570 and/or without openings 522. Layers 402, 404 and 406 can be surrounded by, for example, a tube connected to a side arm which is in fluid communication with a pump and applies a pressure to the exterior of layer 406.

In certain embodiments, heating element 510 is an 18 Ohm resistive heating rod.

In some embodiments, temperature controller 550 is a programmable temperature controller programmed to heat element 510 to about 170° C. over a period of about 20 minutes, hold the temperature at about 170° C. for about two minutes, and then turn off heating element 510.

While certain methods and systems for forming the shaft of an insertion tube device have been described, other systems and methods can also be used.

In some embodiments, tube 520 is formed of a material other than stainless steel. Generally, such a material can withstand the temperature range of the heating element, and has at least some thermal conductivity. This group of materials includes materials such as stainless steel, cast iron, copper, aluminum alloys, quartz, glass, and ceramic material. In other embodiments, the system does not include tube 520.

In embodiments in which a portion of the material of layer 406 is caused to flow into layer 404 by applying pressure from the exterior of layer 406, a vacuum can be applied to the interior of layer 402.

In some embodiments, one or more clamps can be used to hold layers 402, 404 and/or 406 in place when heating layer 406.

In certain embodiments, a layer of a material can be placed around the exterior of layer 406 before forming the shaft. In these embodiments, during heating the additional layer of material tends to reduce in size, thereby applying a pressure to the exterior of layer 406 and assisting in flowing a portion of the melted material of layer 406 into openings in layer 404. This approach can result in layer 406 having a relatively uniform exterior surface. The additional layer of material can be formed of, for example, a heat shrink material. In some embodiments, the additional layer of material has little tendency to stick to the material of layer 406 so that the additional layer of material can be readily removed after formation of the shaft. Examples of materials from which the additional layer can be formed include FEP or Teflon. Optionally, the additional layer of material can be used with the application of an external pressure and/or an internal vacuum.

In certain embodiments, the shaft is prepared without applying a pressure differential across layers 402, 404 and 406 (e.g., without applying an external pressure and without applying an internal vacuum), and the resulting shaft may or may not have some of the material of layer 406 disposed within openings in layer 404 (e.g., layer 406 is bonded to layer 406 along surface 405). In these embodiments, tube 520 can be formed without openings 522.

In some embodiments, the system is heated by applying heat from the exterior of the system. For example, one or more heating elements can be placed adjacent the exterior of layer 406. In certain embodiments, the heating element(s) can encircle the exterior of layer 406. In these embodiments, the system can optionally include heating element 510.

In some embodiments, while the material of layer 406 is in a semi-solid state (e.g., at least partially melted), the exterior of layer 406 is knurled with a tool to texture the surface. Alternately, heating of the assembly can be used to bring out the underlying surface of the exterior layer 406, such as heating to a point where the underlying braid structure of layer 404 shows through layer 406. Texturing the surface can reduce friction between the exterior of the shaft and surfaces with which the exterior of the shaft comes into contact. For example, texturing the surface can reduce friction encountered when inserting the shaft into a body cavity.

In certain embodiments, the exterior surface of shaft 400 (e.g., the exterior surface of layer 406) has an Ra value of at least about 0.5 micrometer (e.g., at least about one micrometer, at least about 10 micrometers, at least about 25 micrometers) and/or at most about 100 micrometers (e.g., at most about 75 micrometers, at most about 50 micrometers) according to DIN 4768 T1.

Other embodiments are also possible.

As an example, the proximal portion of an endoscope can have any of a variety of designs. In some embodiments, the proximal end of an endoscope has a handle body with a strain relief for the insertion tube. The handle body can serve as a housing for several components. The components can include: articulation levers and wheels with or without their associated articulation mechanism (e.g., a drum with a wire around its circumference, a rack and pinion type gear for pushing and/or pulling the articulation wires); an eyepiece for viewing the image transmitted from the distal end of the endoscope (e.g., by a flexible fiber bundle); a video camera (e.g., for transmitting the image to a video monitor); electrical connections for a camera placed at the distal end of the endoscope; a light guide connection that permits the light from an external light source to be transmitted down the insertion tube to the distal end; a venting valve to equalize the pressure within the endoscope when it is disinfected with a pressurized system, such as ethylene oxide; an access port for the working channel of the endoscope; and/or an access port for suction and/or irrigation.

As another example, the distal portion of an endoscope can have any of a variety of designs. In some embodiments, the distal portion of the endoscope has a vertebrae system for articulating the distal end of the scope and/or a mechanism for steering the distal portion of the endoscope (e.g., for bending in a plane at a desired angle, such as an angle that is at most about 140°). The distal portion of the endoscope can also include lenses for capturing an image to be transmitted to the proximal end of the endoscope (e.g., via a fiber optic, via the output of a CCD, via a CMOS imaging chip placed within the distal portion of the endoscope). In certain embodiments, one or more light guides extend to the distal portion of the endoscope (e.g., for transferring light from the light source down the insertion tube length, and illuminating the object under view). The distal portion of the endoscope can also include working channel(s) (e.g., to be used for passing a tool, such as biopsy forceps or a biopsy brush or needle, down the length of the insertion tube, or for suction and/or irrigation). In some embodiments, the distal portion of an endoscope has a directed water jet that sprays water, or other suitable liquid, onto the face of the optics (e.g., to wash away any debris that may accumulate on the optics).

As a further example, the shaft of an insertion tube device can house any of a variety of components. In some embodiments, the shaft houses an image fiber optic bundle, which transmits an optical image. In certain embodiments, the shaft houses electronic wires used to transmit a video signal from the distal end of the endoscope to the proximal end of the endoscope. The shaft can also house light guide fibers, one or more working channels, articulation wires, and/or spring guides.

As another example, the wall of the shaft of an insertion tube device or umbilical may include more or fewer layers of material. For example, the wall can be formed without the layer of braided material or without the monocoil layer. Additionally or alternatively, one or more layers of material can be disposed (e.g., painted) on the exterior surface of layer 406. For example, a series of spaced ring-shaped markings (e.g., ring-shaped markings spaced about every 10 centimeters) can be disposed on the exterior surface of layer 406 and can be used to determine the penetration depth of the insertion tube device during use. The ring-shaped markings may optionally be coated with a material to extend the useful lifetime of the markings.

Moreover, while endoscopes having one shaft have been described, the invention is not so limited. For example, an endoscope may have multiple proximal ends, multiple distal ends, and/or multiple shafts. In certain embodiments, an endoscope may have one proximal end, one distal end, and shafts. In some embodiments, an endoscope may have multiple proximal ends, multiple distal ends, and one shaft. Combinations of these designs may be used.

In addition, while the shafts have been described as being flexible, in some embodiments the shafts can be rigid.

Furthermore, the shafts can be used in various types of endoscopes (e.g., electronic endoscopes, such as electronic endoscopes having a camera and/or charged coupled device at the distal end). The shafts can be also used in insertion tube devices other than endoscopes, such as catheters.

Moreover, the foregoing materials, constructions and methods can be used in tubes and other devices that are not insertion devices. As an example, the umbilical of an insertion device (e.g., an endoscope, a borescope, a fiberscope) can be formed by one of the foregoing constructions (e.g., layers 402, 404 and 406 with or without additional layers) and/or methods.

Other embodiments are in the claims.

What is claimed is:

1. A method for making a flexible shaft or member, comprising:
    disposing a first material adjacent a surface of a base material the base material being between the first material and a second material, the first material being substantially unmelted and the second material forming a structure with openings;
    melting at least a portion of the first material; and
    solidifying the portion of the first material to form a flexible member in which the first material is at least partially bonded to the surface of the base material, wherein said flexible member is devoid of an adhesive material between the base and first materials.

2. The method of claim 1, wherein the flexible member is in the shape of a tube, and the first material at least partially surrounds the base material.

3. The method of claim 1, wherein the flexible member is configured to be inserted into a cavity of a patient.

4. The method of claim 1, wherein the flexible member is a mantle of an endoscope shaft.

5. The method of claim 1, wherein the portion of the first material is melted by exposure to electromagnetic radiation.

6. The method of claim 5, wherein the electromagnetic radiation is selected from the group consisting of infrared radiation and microwave radiation.

7. The method of claim 1, wherein the base material forms a structure with openings, and the method further comprises disposing some of the first material in the openings of the base material.

8. The method of claim 7, further comprising applying a pressure differential across the flexible member when the portion of the first material is melted to dispose the first material in the openings.

9. The method of claim 1, further comprising, before melting the portion of the first material, disposing a third material adjacent the first material so that the first material is between the base and third materials.

10. The method of claim 9, wherein during melting of the portion of the first material, the third material exerts a pressure against the first material so that some of the first material is disposed in the openings of the base material.

11. The method of claim 1, further comprising burnishing a surface of the first material when the portion of the first material is melted.

12. The method of claim 11, wherein burnishing the first material textures the surface of the first material.

13. The method of claim 1, wherein the flexible member has an interior and an exterior, and the method further comprises:
disposing a heating element within the interior of the flexible member; and
heating the heating element to melt the portion of the first material.

14. The meted of claim 13, further comprising, prior to disposing the hearing element within the interior of the flexible member, disposing the heating element in a tubing so that, after disposing the healing element within the interior of the flexible member, both the heating element and the tubing are disposed within the interior of the flexible member.

15. The method of claim 1, wherein the flexible member has an interior and an exterior, and the method further comprises:
disposing a heating element outside the exterior of the flexible member; and
heating the heating element to melt the portion of the first material.

16. The method of claim 1, wherein the first material is bonded to the base material at discrete locations within the base material.

17. The method of claim 1, wherein the first material comprises a polymer.

18. The method of claim 17, wherein the polymer is selected from the group consisting of urethanes, polyesters, olefinic thermoplastic elastomers, chlorinated polyethylene-based thermoplastic elastomers, polyvinyl chlorides, 1,2-butadienes, polystyrenes, fluoropolymers, silicon rubbers and combinations thereof.

19. The method of claim 1, wherein the second material is in the form of a monocoil.

20. The method of claim 1, wherein the base material is m the form of a braided material.

21. The method of claim 1, wherein the flexible member is an umbilical of an insertion device.

22. A method for making a flexible shaft or member, comprising:
disposing a first material adjacent a surface of a base material, the base material having openings and being between the first material and a second material, the first material being substantially unmelted; and
bonding at least a portion of the first material to the base material to form a flexible member without extruding the first material onto a surface of the second material and without including an adhesive material between the base and first materials.

23. The method of claim 22, wherein the flexible member is in the shape of a tube, and the first material at least partially surrounds the base material.

24. The method of claim 22, wherein the flexible member is configured to be inserted into a cavity of a patient.

25. The method of claim 22, wherein the flexible member is a mantle of an endoscope shaft.

26. The method of claim 22, further comprising:
melting the portion of the first material; and
solidifying the portion of the first material to bond the portion of the first material to the surface of the base material.

27. The method of claim 22, wherein the base material forms a structure with openings, and bonding the portion of the first material to the surface of the base material includes disposing some of the first material in the openings of the base material.

28. The method of claim 27, further comprising applying a pressure differential across the flexible member to dispose the first material in the openings.

29. The method of claim 22, further comprising, before bonding the portion of the first material to the surface of the base material, disposing a third material adjacent the first material so that the first material is between the base and third materials.

30. The method of claim 29, wherein the base material forms a structure with openings, and, during bonding of the portion of the first material to the surface of the base material, the second third material exerts a pressure against the first material so that some of the first material is disposed in the openings of the base material.

31. The method of claim 22, further comprising:
melting the portion of the first material during bonding; and
burnishing a surface of the first material when the portion of the first material is melted.

32. The method of claim 31, wherein burnishing the first material textures the surface of the first material.

33. The method of claim 22, wherein the flexible member has an interior and an exterior, and the method further comprises:
disposing a heating element within the interior of the flexible member; and
heating the heating element to melt the portion of the first material.

34. The method of claim 33, further comprising, prior to disposing the heating element within the interior of the flexible member, disposing the heating element in a tubing so that, after disposing the heating element within the interior of the flexible member, both the heating element and the tubing are disposed inside the flexible member.

35. The method of claim 22, wherein the flexible member has an interior and an exterior, and the method further comprises:

disposing a heating element outside the exterior of the flexible member; and heating the heating element to melt the portion of the first material.

36. The method of claim 22, wherein the first material is bonded to the base material at discrete locations within the base material.

37. The method of claim 22, wherein the first material comprises a polymer.

38. The method of claim 37, wherein the polymer is selected from the group consisting of urethanes, polyesters, olefinic thermoplastic elastomers, chlorinated polyethylene-based thermoplastic elastomers, polyvinyl chlorides, 1,2-butadienes, polystyrene; fluoropolymers, silicon rubbers and combinations thereof.

39. The method of claim 22, wherein the second material is in the form of a monocoil.

40. The method of claim 22, wherein the base material is in the form of a braided material.

41. The method of claim 22, wherein the flexible member is an umbilical of an insertion device.

42. A method for making a flexible shaft or member, comprising:

disposing a first material adjacent a surface of a base material which is between the first material and a second material, the first material being substantially unmelted, and the second material forming a structure with openings;

melting at least a portion of the first material; and solidifying the portion of the first material so that the first, second, and base materials form a shaft of an insertion tube device in which the first material is at least partially bonded to the surface of the base material, wherein said shaft is devoid of an adhesive material between the base and first materials.

43. The method of claim 42, wherein the shaft is a mantle of an endoscope.

44. A method for making a flexible shaft or member, comprising:

disposing a first material adjacent a surface of a base material which is between the first material and a second material the first material being substantially unmelted; and bonding at least a portion of the first material to the surface of the base material to form a shaft of an insertion tube device without extruding the first material onto a surface of the second material and without including an adhesive material between the base and first materials.

45. The method of claim 44, wherein the shaft is a mantle of an endoscope.

46. A flexible member, comprising:

a base material having a surface;

a first material; and a second material forming a structure with openings, wherein the base material is between the first and second materials, and a portion of the first material is bonded to the base material at discrete locations, and the flexible member is devoid of an adhesive material between the base and first materials and is configured to be inserted into a cavity of a patient.

47. The flexible member of claim 46, wherein the base material has openings, and a portion of the first material is disposed within the openings of the base material.

48. The flexible member of claim 46, wherein the flexible member is in the shape of a tube, and the first material at least partially surrounds the base material.

49. The flexible member of claim 46, wherein the flexible member is a mantle of an endoscope shaft.

50. The flexible member of claim 46, wherein the flexible member has a diameter of at most about 30 millimeters.

51. The flexible member of claim 46, wherein the flexible member has a length of at most about 10 meters.

52. The flexible member of claim 46, wherein the first material comprises a polymer.

53. The flexible member of claim 52, wherein the polymer is selected from the group consisting of urethanes, polyesters, olefinic thermoplastic elastomers, chlorinated polyethylene-based thermoplastic elastomers, polyvinyl chlorides, 1,2-butadienes, polystyrenes, fluoropolymers, silicon rubbers and combinations thereof.

54. The flexible member of claim 46, wherein the second material is in the form of a monocoil.

55. The flexible member of claim 46, wherein the base material is in the form of a braided structure.

56. The flexible member of claim 46, wherein an exterior surface of the first material is textured.

57. The flexible member of claim 46, further comprising a third material, the first material being between the base and third materials.

58. The flexible member of claim 57, wherein the third material comprises a heat shrink material.

59. The flexible member of claim 57, wherein the base material has a second surface adjacent to the second material, and at least some of the first material extends beyond the second surface of the base material.

60. The flexible member of claim 46, wherein the flexible member is an umbilical of an insertion device.

61. A shaft of an insertion tube device, comprising:

a base material having a surface;

a first material; and a second material forming a structure with openings, wherein the base material is between the first and second materials, and a portion of the first material is bonded to the base material at discrete locations and the shaft is devoid of an adhesive material between the base and first materials and is configured to be inserted into a cavity of a patient.

62. The shaft of claim 61, wherein the base material has openings, and the second portion of the first material is disposed within the openings of the base material.

63. The shaft of claim 61, wherein the shaft is flexible.

64. The shaft of claim 61, wherein the shaft is a mantle of an endoscope.

65. A method for making a flexible shaft or member, comprising:

disposing a first material adjacent a surface of a second material, the first material being substantially unmelted and the second material forming a structure with openings;

melting at least a portion of the first material into the openings of the second material; and solidifying the portion of the first material so that the first and second materials form a flexible member in which the first material is at least partially disposed within the openings in the base layer.

66. A method for making a flexible shaft or member, comprising:

disposing a first material adjacent a surface of a base material, the first material being substantially unmelted and the base material having openings; and bonding at least a portion of the first material within the openings of the base material to form a flexible member without extruding the first material onto a surface of a second material, the base material being between the first and second materials.

67. A method for making a flexible shaft or member, comprising:
disposing a first material adjacent a surface of a second material, the first material being substantially unmelted and the second material forming a structure with openings;
melting at least a portion of the first material into the openings of the base material; and
solidifying the portion of the first material so that the first and second materials form a shaft of an insertion tube device in which the first material is at least partially disposed within the openings in the second layer.

68. A method for making a flexible shaft or member, comprising:
disposing a first material adjacent a surface of a base material, the first material being substantially unmelted and the base material having openings; and
bonding at least a portion of the first material within the openings of the base material to form a shaft of an insertion tube device without extruding the first material onto a surface of a second material, the base material being between the first and second materials.

69. A flexible member, comprising:

a base material having openings;

a first material; and a second material having a surface, wherein the base material is between the first and second materials, and a portion of the first material is disposed within the openings of the base material without contacting the a surface of the second material, and the flexible member is devoid of an adhesive material between the base and first materials and is configured to be inserted into a cavity of a patient.

* * * * *